United States Patent [19]

Richter et al.

[11] Patent Number: 5,068,361
[45] Date of Patent: Nov. 26, 1991

[54] PREPARATION OF CAPROLACTONE

[75] Inventors: Wolfgang Richter, Wachenheim; Rolf Fischer, Heidelberg; Uwe Vagt, Speyer, all of Fed. Rep. of Germany

[73] Assignee: BASF Aktiengesellschaft, Ludwigshafen, Fed. Rep. of Germany

[21] Appl. No.: 587,155

[22] Filed: Sep. 20, 1990

Related U.S. Application Data

[63] Continuation of Ser. No. 365,126, Jun. 12, 1989, abandoned.

[30] Foreign Application Priority Data

Jul. 8, 1988 [DE] Fed. Rep. of Germany ....... 3823213

[51] Int. Cl.$^5$ ............................................. C07D 309/10
[52] U.S. Cl. ..................................................... 549/273
[58] Field of Search .................................. 549/266, 273

[56] References Cited

U.S. PATENT DOCUMENTS

| | | |
|---|---|---|
| 3,189,619 | 6/1965 | Aldridge et al. . |
| 3,317,563 | 5/1967 | Horlenko et al. .................. 549/266 |
| 3,429,852 | 2/1969 | Skoultchi et al. ..................... 260/47 |
| 3,523,955 | 8/1970 | Lantz et al. ......................... 549/266 |
| 4,634,791 | 1/1987 | Meier et al. ......................... 560/163 |
| 4,709,058 | 11/1987 | Cahill, Jr. ............................. 549/266 |

FOREIGN PATENT DOCUMENTS

| | | |
|---|---|---|
| 0246848 | 11/1987 | European Pat. Off. . |
| 1115702 | 5/1968 | United Kingdom ............... 549/266 |
| 1153364 | 5/1969 | United Kingdom ............... 549/266 |

OTHER PUBLICATIONS

*Chemical Abstracts, vol. 78, entry 125138t (1973).*

*Primary Examiner*—Richard L. Raymond
*Assistant Examiner*—Mark W. Russell
*Attorney, Agent, or Firm*—Keil & Weinkauf

[57] ABSTRACT

Caprolactone is prepared by a process in which a 6-hydroxycaproic ester in vapor form is passed, together with an inert carrier gas, at from 150° to 450° C., over a fixed-bed or fluidized-bed oxidic catalyst.

5 Claims, No Drawings

PREPARATION OF CAPROLACTONE

This application is a continuation of application Ser. No. 365,126, filed on June 12, 1989, now abandoned.

U.S. Pat. No. 3,189,619 discloses a process in which a 6-hydroxycaproic ester is reacted in a first stage with a trialkyl borate and the reaction product is then converted into caprolactone by heating at from 200° to 250° C. under reduced pressure. This process is expensive and unsuitable for industrial use.

In another process, disclosed in French Patent 1,474,903, a 6-hydroxycaproic ester is heated to 150-350° C. in the presence of an oxide, such as magnesium oxide, zinc oxide, cadmium oxide, alumina or titanium dioxide, in the liquid phase under reduced pressure, and caprolactone is distilled off continuously. This process has the disadvantage that the catalysts used are rapidly deactivated and can be regenerated only by an expensive procedure.

It is an object of the present invention to provide a process for the preparation of caprolactone from a 6-hydroxycaproic ester, which process can be carried out by a simple continuous procedure and in which the catalysts used have a fairly long life and can easily be regenerated.

We have found that this object is achieved by a process for the preparation of caprolactone, in which a 6-hydroxycaproic ester is heated at from 150° to 450° C. in the presence of an oxidic catalyst, wherein 6-hydroxycaproic ester vapor is passed, together with a carrier gas, over a fixed-bed or fluidized-bed oxidic catalyst.

The novel process has the advantages that it can be carried out by a simple continuous procedure and that the catalysts used are not contaminated with residues, have a fairly long life and can be regenerated in a simple manner.

Preferred 6-hydroxycaproic esters are derived from alkanols of 1 to 12 carbon atoms, cycloalkanols of 5 to 7 carbon atoms, aralkanols of 7 to 8 carbon atoms or phenols of 6 to 8 carbon atoms. Particularly preferred starting materials are $C_1$-$C_4$-alkyl 6-hydroxycaproates, in particular methyl 6-hydroxycaproate. Examples are methyl 6-hydroxycaproate, ethyl 6-hydroxycaproate, n-propyl 6-hydroxycaproate, isopropyl 6-hydroxycaproate, n-butyl 6-hydroxycaproate and 2-ethylhexyl 6-hydroxycaproate, cyclohexyl 6-hydroxycaproate and phenyl 6-hydroxycaproate.

An essential feature of the invention is that a 6-hydroxycaproate ester in vapor form is passed, together with a carrier gas, over a fixed-bed or fluidized-bed oxidic catalyst.

6-Hydroxycaproic esters are advantageously vaporized at from 180° to 300° C. It has proven advantageous if solvents which are inert under the reaction conditions, such as esters, eg. dioxane or tetrahydrofuran, are also vaporized simultaneously. Advantageously, from 50 to 90% strength by weight solutions of 6-hydroxycaproic esters in such solvents are used.

Examples of inert carrier gases are nitrogen, carbon dioxide and argon. Nitrogen is preferably used as the carrier gas. As a rule, from 10 to 30 moles of carrier gas are used per mole of 6-hydroxycaproic ester vapor.

Examples of suitable oxidic catalysts are oxides of elements of main groups 2 to 5 or subgroups 1 to 8 of the Periodic Table or oxides of rare earth metals or mixtures thereof. Examples are magnesium oxide, zinc oxide, boron trioxide, titanium dioxide, silica, tin dioxide, bismuth oxide, copper oxide, lanthanum oxide, zirconium dioxide, vanadium oxides, chromium oxides, tungsten oxides, iron oxides, cerium oxides and neodynium oxides. Silica, for example in the form of silica gel, kieselguhr or quartz, alumina, for example in the form of γ-alumina, and zinc oxide, boron trioxide and titanium dioxide are preferably used. Silica has proven particularly suitable.

In one procedure, the oxidic catalyst is arranged as a fixed bed in the reaction zone and the mixture of the 6-hydroxycaproic ester vapor and the carrier gas is passed over the said catalyst. In another procedure, the catalyst is in the form of a fluidized bed. Advantageously, a space velocity of from 0.01 to 40, in particular from 0.1 to 20, g of hydroxycaproic ester per g of catalyst per hour is maintained.

The reaction is carried out at from 150° to 450° C., preferably from 200° to 400° C., in particular from 300° to 350° C., in general under atmospheric pressure. However, it is also possible to use slightly reduced pressure, for example down to 500 mbar, or slightly superatmospheric pressure, for example up to 1.2 bar.

The process according to the invention is carried out, for example, by vaporizing the 6-hydroxycaproic ester, if necessary as a mixture with the stated solvents, and passing it, together with one of the stated inert gases, at the stated reaction temperatures, into a fluidized-bed catalyst having the stated composition. The reacted mixture is condensed using suitable cooling apparatuses and then worked up by distillation in a known manner. Unconverted 6-hydroxycaproic esters are advantageously reused for the reaction.

The caprolactone obtainable by the process of the invention is suitable for the preparation of polyesters.

The Examples which follow illustrate the process according to the invention. In the Examples 6-HCE is methyl 6-hydroxycaproate and CLO is caprolactone.

EXAMPLE 1

10 ml/h of 6-HCE are pumped into an evaporator and are passed from there in gaseous form, together with 3 l of nitrogen, over 10 g of the catalyst stated in Table 1 (in each case 1-3 mm chips), at from 250° to 350° C. The gaseous reacted mixtures were condensed in cold traps, weighed, and analyzed by gas chromatography. Table 1 shows the yield as a function of temperature and catalyst after an experimental time of 4 hours in each case.

TABLE 1

| No. | Catalyst | Temp. [°C.] | Conversion [mol %] | Yield of CLO [mol %] |
|---|---|---|---|---|
| 1 | Silica | 250 | 60 | 55 |
| 2 | Silica | 330 | 89 | 82 |
| 3 | Silica | 350 | 90 | 79 |
| 4 | Titanium dioxide | 250 | 53 | 44 |
| 5 | Alumina + 5% of phosphoric acid | 250 | 91 | 40 |

EXAMPLE 2

10 ml/h of 6-HCE were vaporized at about 300° C. and passed, together with 30 l of nitrogen, over 45 g of a fluidized-bed silica catalyst having a particle size of from 0.1 to 0.3 mm (reaction temperature 330° C.). The gaseous reacted mixture was condensed in cold traps, weighed, an analyzed by gas chromatography. The reacted mixtures were collected over a total experimental time of 72 hours (total feed of 6-HCE: 757 g). The liquid reacted mixture (737 g) contained 66% by weight of CLO, 10% by weight of 6-HCE and 19% by weight of methanol, according to gas chromatographic analysis.

To work up the mixture, the low boilers in the reacted mixture (methanol) was stripped off under reduced pressure and the residue was subjected to fractional distillation under reduced pressure.

Yield: 437 g (80% of theory) of pure caprolactone of boiling point 62° C./0.3 mbar.

EXAMPLE 3

500 g of γ-alumina spheres (1–3 mm diameter, commercial product from Norton, Ohio) were impregnated for 4 hours with 5% by weight of phosphoric acid solution in water and then calcined for 20 hours at 300° C.

40 g/h of 6-HCE were vaporized at 180–190° C. and were passed, together with 110 l of nitrogen, over 400 g of this alumina/phosphoric acid catalyst (reaction temperature 350° C.). The gaseous reacted mixture was condensed in cold traps, weighed, and analyzed by gas chromatography. The reacted mixtures were collected over a total experimental time of 8 hours (total feed: 320 g of 6-HCE). The liquid reacted mixture (310 g) contained 68% by weight of CLO, 10% by weight of 6-HCE and 19% by weight of methanol, according to gas chromatographic analysis.

To work up the mixture, the low boilers in the reacted mixture (methanol) were stripped off under reduced pressure and the residue was treated with calcium carbonate and then subjected to fractional distillation under reduced pressure.

Yield: 202 g (80% of theory) of pure caprolactone of boiling point 62° C./0.3 mbar.

EXAMPLE 4

10 ml/h of 6-HCE were vaporized at about 300° C. and passed, together with 30 l of nitrogen, over 45 g of a fluidized-bed silica catalyst having a particle size of from 0.1 to 0.3 mm (reaction temperature 330° C.).

The gaseous reacted mixture was condensed in cold traps, weighed, and analyzed by gas chromatography. The reacted mixtures were collected over a total experimental time of 36 hours (total feed: 380 g of 6-HCE). The liquid reacted mixture (362 g) contained 66% by weight of CLO, 10% by weight of 6-HCE and 19% by weight of methanol, according to gas chromatographic analysis.

For further working up, the low boilers in the reacted mixture (methanol, were stripped off under reduced pressure and the residue (310 g) was passed over the fluidized-bed silica catalyst under the same conditions as those stated above.

The gaseous reacted mixture was again condensed in cold traps, weighed, and analyzed by gas chromatography. The liquid reacted mixture (295 g) now contained 88% by weight of CLO, 1% by weight of 6-HCE and 2% by weight of methanol, according to gas chromatographic analysis.

To work up the mixture, the low boilers in the reacted mixture (methanol) were stripped off under reduced pressure and the residue was subjected to fractional distillation under reduced pressure.

Yield: 255 g (86% of theory) of pure caprolactone of boiling point 62° C./0.3 mbar.

EXAMPLE 5

10 ml/h of 6-HCE were vaporized at about 300° C. and passed, together with 25 l of nitrogen, over 45 g of a fluidized-bed silica catalyst having a particle size of from 0.1 to 0.3 mm (reaction temperature 330° C.).

The gaseous reacted mixture was condensed in cold traps over an experimental time of 168 hours, weighed, and analyzed by gas chromatography. The liquid reacted mixture contained throughout 71% by weight of CLO, 5% by weight of 6-HCE and 20% by weight of methanol (corresponding to a CLO yield of 89% of thebry), according to gas chromatographic analysis.

We claim:

1. A process for the preparation of caprolactone which comprises: passing a $C_1$–$C_4$ alkyl 6-hydroxycaproic ester in vapor form, together with an inert carrier gas, at from 150° to 450° C., over a fixed-bed or fluidized-bed oxidic catalyst, wherein the catalyst used is silica, titanium dioxide or a mixture thereof.

2. A process as claimed in claim 1, wherein a temperature of from 300° to 350° C. is maintained.

3. A process as claimed in claim 1, wherein the catalyst used is silica.

4. A process as claimed in claim 1, wherein a space velocity of from 0.1 to 20 g of 6-hydroxycaproic ester per g of catalyst per hour is maintained.

5. A process as claimed in claim 1, wherein from 10 to 30 moles of carrier gas are used per mole of 6-hydroxycaproic ester.

* * * * *